(12) United States Patent
Huang et al.

(10) Patent No.: US 12,339,240 B2
(45) Date of Patent: Jun. 24, 2025

(54) METHOD FOR DETECTION OF SOIL HEAVY METAL POLLUTION USING UNMANNED AERIAL VEHICLE (UAV) AND X-RAY FLUORESCENCE (XRF) TECHNOLOGY

(71) Applicant: UNIVERSITY OF ELECTRONIC SCIENCE AND TECHNOLOGY OF CHINA, Chengdu (CN)

(72) Inventors: Fang Huang, Chengdu (CN); Shuying Peng, Chengdu (CN); Hao Yang, Chengdu (CN); Shengyi Chen, Chengdu (CN)

(73) Assignee: UNIVERSITY OF ELECTRONIC SCIENCE AND TECHNOLOGY OF CHINA, Chengdu (CN)

( * ) Notice: Subject to any disclaimer, the term of this patent is extended or adjusted under 35 U.S.C. 154(b) by 447 days.

(21) Appl. No.: 17/719,859

(22) Filed: Apr. 13, 2022

(65) Prior Publication Data
US 2022/0365007 A1    Nov. 17, 2022

(30) Foreign Application Priority Data
May 8, 2021    (CN) .......................... 202110498045.6

(51) Int. Cl.
    *G01N 23/223*    (2006.01)
    *B64U 101/00*    (2023.01)
            (Continued)

(52) U.S. Cl.
    CPC .......... *G01N 23/223* (2013.01); *G01C 21/20* (2013.01); *G01N 33/24* (2013.01); *G01S 19/45* (2013.01);
            (Continued)

(58) Field of Classification Search
    CPC .......... G01N 23/223; G01N 2223/076; G01N 2223/507; G01N 2223/616; G01N 33/24;
            (Continued)

(56) References Cited

U.S. PATENT DOCUMENTS 4,848,590 A  *  7/1989  Kelly ................... B07C 5/3427
                                                    209/564
7,436,926 B2 * 10/2008  Matoba ............... G01N 23/223
                                                    378/45
            (Continued)

*Primary Examiner* — Luis A Martinez Borrero
(74) *Attorney, Agent, or Firm* — PERRY + CURRIER INC.

(57) ABSTRACT

The present disclosure provides a method for detection of soil heavy metal pollution using an unmanned aerial vehicle (UAV) and an X-ray fluorescence (XRF) technology. Based. Based on hardware equipment such as the UAV, XRF analyzer, and embedded equipment, the present disclosure develops an altitude hold module of the system and a ground-contact monitoring module, and assists the UAV to achieve safe and accurate fixed-point hovering, and develops a driving device for data acquisition to replace manual control and realize the automatic acquisition of XRF data. The data inversion method is realized by using embedded equipment, and after the data is acquired by the portable XRF analyzer near the ground, the algorithm research of inversion processing of contents of heavy metal elements in soil is realized, such that the portable XRF analyzer can automatically and accurately detect the contents of heavy metals in soil at a certain distance.

9 Claims, 9 Drawing Sheets

(51) Int. Cl.
*G01C 21/20* (2006.01)
*G01N 33/24* (2006.01)
*G01S 19/45* (2010.01)
*G05D 1/00* (2024.01)

(52) U.S. Cl.
CPC ........ *G05D 1/101* (2013.01); *B64U 2101/00* (2023.01); *G01N 2223/076* (2013.01); *G01N 2223/507* (2013.01); *G01N 2223/616* (2013.01)

(58) Field of Classification Search
CPC ........ G01C 21/20; G01S 19/45; G05D 1/101; B64U 2101/00
USPC ............................................................. 701/4
See application file for complete search history.

(56) References Cited

U.S. PATENT DOCUMENTS

| | | | | | |
|---|---|---|---|---|---|
| 7,858,385 | B2* | 12/2010 | Warner | ............ | G01N 33/54373 436/103 |
| 8,560,146 | B2* | 10/2013 | Kwon | ................. | G05D 1/0044 701/4 |
| 9,465,036 | B2* | 10/2016 | Winnik | ............... | G01N 33/6848 |
| 10,031,148 | B2* | 7/2018 | Szudajski | ............... | B25J 9/1679 |
| 10,107,770 | B2* | 10/2018 | Weindorf | ........... | G01N 21/3563 |
| 10,268,198 | B2* | 4/2019 | Mantripragada | ...... | G05D 1/104 |
| 10,488,860 | B1* | 11/2019 | Koch | .................... | G06F 16/9537 |
| 10,527,600 | B2* | 1/2020 | Warner | ................ | G01N 33/182 |
| 10,628,757 | B2* | 4/2020 | Du | ........................ | G06Q 10/00 |
| 10,703,488 | B2* | 7/2020 | Fagundes | ............... | B64D 45/00 |
| 10,800,315 | B2* | 10/2020 | Kanck | ....................... | B60P 1/52 |
| 11,100,357 | B2* | 8/2021 | Wang | .................... | G06V 10/993 |
| 11,231,726 | B2* | 1/2022 | Liu | ....................... | G05D 1/0088 |
| 11,573,224 | B2* | 2/2023 | Zahler | ................. | G01N 23/223 |
| 11,592,407 | B2* | 2/2023 | Segal | .................. | G01N 23/2204 |
| 11,598,759 | B2* | 3/2023 | Warner | ................ | G01N 23/223 |
| 11,698,354 | B1* | 7/2023 | Zhang | .................. | G01N 33/24 378/44 |
| 11,761,938 | B2* | 9/2023 | Potyrailo | ............... | B64U 50/19 73/31.03 |
| 11,867,645 | B2* | 1/2024 | Grof | ................... | G01N 23/223 |
| 11,893,834 | B2* | 2/2024 | Forejt | ....................... | B64F 5/60 |
| 11,947,354 | B2* | 4/2024 | Koch | ....................... | G06F 16/29 |
| 2007/0003008 | A1* | 1/2007 | Warner | ................ | G01N 23/223 378/44 |
| 2007/0269004 | A1* | 11/2007 | Matoba | ................ | G01N 23/223 378/45 |
| 2008/0180691 | A1* | 7/2008 | Hays | ........................ | G01S 17/95 356/519 |
| 2009/0055101 | A1* | 2/2009 | Strubel | ............... | H01J 49/0036 702/19 |
| 2010/0278312 | A1* | 11/2010 | Ortiz | .................... | G01N 23/223 378/195 |
| 2012/0028273 | A1* | 2/2012 | Straume | ............... | C12Q 1/6816 435/7.1 |
| 2012/0046203 | A1* | 2/2012 | Walsh | ................ | G01N 35/0098 422/69 |
| 2013/0170613 | A1* | 7/2013 | Utaka | .................. | G01N 23/223 378/46 |
| 2013/0182819 | A1* | 7/2013 | Dvorkin | ............... | G01N 23/046 378/5 |
| 2013/0191046 | A1* | 7/2013 | Henning | ............... | G01N 23/083 702/50 |
| 2014/0131165 | A1* | 5/2014 | Johnson, Jr. | ......... | G01N 33/222 198/339.1 |
| 2014/0211914 | A1* | 7/2014 | Vigliante | ........... | G01N 21/9501 378/49 |
| 2015/0347647 | A1* | 12/2015 | Osborne | ................ | B09C 1/002 703/6 |
| 2016/0110835 | A1* | 4/2016 | Wu | ........................ | G06F 17/18 705/325 |
| 2016/0187313 | A1* | 6/2016 | Szudajski | ............ | G01N 23/046 250/256 |
| 2016/0341678 | A1* | 11/2016 | Peterson | ............... | G01N 33/487 |
| 2017/0122888 | A1* | 5/2017 | Heckner | ............... | G01N 23/223 |
| 2017/0122889 | A1* | 5/2017 | Weindorf | ............. | G01N 21/359 |
| 2019/0120807 | A1* | 4/2019 | Warner | ................ | G01N 33/182 |
| 2019/0351804 | A1* | 11/2019 | Kanck | ....................... | B60P 3/14 |
| 2020/0088707 | A1* | 3/2020 | Warner | ............. | G01N 33/1813 |
| 2020/0278346 | A1* | 9/2020 | Zahler | ............. | G01N 33/54373 |
| 2021/0215590 | A1* | 7/2021 | Li | ........................... | G01N 33/24 |
| 2023/0204526 | A1* | 6/2023 | Zhang | ................. | G01N 23/223 378/44 |
| 2024/0035991 | A1* | 2/2024 | Li | ........................... | G01N 33/24 |

* cited by examiner

METHOD FOR DETECTION OF SOIL HEAVY METAL POLLUTION USING UNMANNED AERIAL VEHICLE (UAV) AND X-RAY FLUORESCENCE (XRF) TECHNOLOGY

CROSS REFERENCE TO RELATED APPLICATION

This patent application claims the benefit and priority of Chinese Patent Application No. 202110498045.6, filed on May 8, 2021, the disclosure of which is incorporated by reference herein in its entirety as part of the present application.

TECHNICAL FIELD

The present disclosure belongs to the field of detection of soil heavy metal pollution, and in particular, relates to a method for rapid detection of soil heavy metal pollution in a large area based on a combination of an unmanned aerial vehicle (UAV) technology and an X-ray fluorescence (XRF) technology.

BACKGROUND ART

As the most important material basis for human survival and development, soil is the basic guarantee for all human activities. In recent years, serious soil heavy metal pollution has seriously threatened the growth quality of animals and plants. The prevention and control of soil heavy metal pollution has always been a research hotspot. The Communist Party of China and the government of China attach great importance to the construction of ecological civilization and food security. The prerequisite for the prevention and control of soil heavy metal pollution is to detect and evaluate the pollution situation. A necessary prerequisite for the prevention and control of soil pollution is to find out the types and contents of heavy metal elements in the soil. Targeted pollution control work can be carried out with a clear understanding of the current situation of soil heavy metal pollution, but soil heavy metal pollution has the characteristics of long-term concealment, difficult control, and long cycle, and it is difficult to achieve early detection, early prevention, and early control. In practical applications, it is usually necessary to carry out rapid and comprehensive detection and risk assessment of heavy metal pollution in the whole soil in a large area.

The detection of soil heavy metal pollution has long been an important research field. Common detection methods for heavy metals in the soil include the chemical analysis technology, the hyperspectral technology, and the XRF technology. The chemical method has high measurement accuracy and can accurately reflect the types and contents of most heavy metal elements in the soil. However, in the chemical method, soil samples need to be obtained from the field and corresponding chemical analysis is carried out in the laboratory. The whole process takes a long time, and the results cannot be obtained quickly. The hyperspectral detection of heavy metals has a wide spectral range and can quickly obtain spectral data in a large area, but the inversion accuracy of this technical method is usually low, and a series of sophisticated equipment is required. The actual process of analyzing the content of heavy metals in the soil in an area is complicated, and the detection cost is high. The XRF technology can rapidly and effectively detect the content of heavy metals in the soil, and can be used in soil heavy metal pollution monitoring and pollution remediation assessment, and because of its significant advantages, the XRF technology has the potential to replace traditional laboratory analysis methods under certain conditions.

X-rays are electromagnetic radiation with wavelengths between ultraviolet light and γ-rays, and have extremely strong penetrating ability. After nearly ten years of continuous development, XRF spectroscopic analysis of element types and contents has become a widely used analysis technology. For example, the XRF technology is playing an important role in mining, building materials, metallurgy, environmental protection, food hygiene, and non-ferrous metals. The XRF technology has many unique advantages. It can analyze multiple metal elements at the same time without destroying the properties of the sample. The analysis process is rapid and convenient, and the detection results are stable and reliable. The current XRF analyzer usually needs to be hand-held for detection. It can rapidly and accurately detect soil heavy metal pollution at a certain point in the field, but it is difficult to rapidly complete the overall detection of soil heavy metal pollution in a large area.

The UAV technology has developed rapidly in recent years. Due to its low cost, flexible flight, and small terrain constraints, the application field of UAV is being continuously expanded. It is playing an increasingly important role in various disciplines such as emergency rescue and disaster relief, social security, environmental monitoring, and agricultural plant protection. The application capability of the UAV can be further improved by carrying the embedded equipment on the UAV as the autonomous control and data processing center of the UAV. Soil monitoring using the UAV has shown the advantages of high data quality, and convenient and rapid acquisition in agricultural research, so it is worth considering the role of the UAV in the field of detection of soil heavy metal pollution.

Several key problems need to be solved in the research of systems for detection of soil heavy metal pollution based on the existing UAV and XRF analyzer: (1) in terms of the UAV, at present, the general UAV and its supporting software can only complete the task planning and flight such as altitude holding and velocity holding in an area, and cannot realize the function of UAV descending at the task point and hovering accurately near the ground to acquire data; (2) in terms of the XRF analyzers, first, the current portable XRF analyzers usually need to be used on the ground and cannot meet the needs of near-ground detection under the UAV platform, and the current commercial portable XRF analyzers have the problem that they need to be hand-held and cannot automatically complete data acquisition.

SUMMARY

An objective of the present disclosure is to provide a method for rapid detection of soil heavy metal pollution by UAV-borne XRF in order to solve the problems existing in the background art. Aiming at the severe situation of soil heavy metal pollution in China and the actual demand for a method for regional, rapid, and convenient detection of soil heavy metal pollution, the method combines the UAV technology and the XRF technology, and makes full use of the advantages of both. UAV flight control and data acquisition and processing are realized through embedded equipment, and rapid and automatic detection of soil heavy metal pollution in a large area is realized. Software and hardware cooperate to form the method for rapid detection of soil heavy metal pollution by UAV-borne XRF.

A method for detection of soil heavy metal pollution using an unmanned aerial vehicle (UAV) and an X-ray fluorescence (XRF) technology includes the following steps:

Step 1, uniformly selecting enough sampling points in an area to be detected using an XRF analyzer, and detecting each sampling point respectively near the ground and on the ground to obtain content data of a set of metal elements to be detected;

Step 2, performing data check and data preprocessing, where after data acquisition is completed, a scatter plot is drawn from known data for data check, obviously wrong data is eliminated, and a fitting degree n of a polynomial is preliminarily determined according to a preliminary image;

Step 3, calculating polynomial fitting functions with highest degrees of n−1 and n and the sum of squared errors successively;

Step 4, if a reduction amount of the sum of squared errors of the last fitting function compared with the sum of squared errors of the previous fitting function is greater than a set threshold, continuing to calculate the fitting function with a highest order greater than n successively until a reduction amount of the final sum of squared errors compared with the sum of squared errors of the previous fitting function is less than the set threshold;

Step 5, recording and saving a fitting function corresponding to a minimum sum of squared errors as a final inversion model; and Step 6, acquiring, by the UAV-borne XRF analyzer, soil data near the ground, inverting the acquired soil data according to the inversion model to obtain accurate content data of heavy metal elements in soil, and recording and saving the inverted data.

Further, in step 6, a method for controlling an UAV when the UAV-borne XRF analyzer acquires the data may be as follows:

Step 1.1, initializing and self-checking each module of a system to ensure that each module of the system works normally;

Step 1.2, planning an UAV flight task route for soil heavy metal pollution monitoring, and constructing a task queue;

Step 1.3, enabling the UAV to take off: when the task queue is valid, enabling the UAV to take off to a specified altitude H, where H is the set plane flight altitude of the UAV;

Step 1.4, performing automatic control of plane flight of the UAV: controlling the UAV to fly over the next task point, where a flight path of an operation plane of the UAV may be a straight line from a point A to a point B, and the altitude may remain unchanged at the flight altitude H;

Step 1.5, performing automatic control of a descending process of the UAV: in order to acquire valid data, controlling the UAV to descend to a predetermined altitude and hover for completion of data acquisition;

Step 1.6, enabling the UAV to hover and performing data acquisition: keeping the UAV hovering at an altitude of $h_2$ accurately until the data acquisition is completed, and repeating step 1.4 until the data acquisition is completed for all task points in the task queue; and Step 1.7, enabling the UAV to return and land: automatically controlling the UAV to return to coordinates of a take-off point and land.

Further, a specific method of step 3 may be as follows:

Assuming that there are n+1 linearly independent continuous functions:

$\varphi_0(x), \varphi_1(x), \ldots, \varphi_n(x)$, where $\varphi_k(x) = x^k$, k=1, 2, ..., n, $$p(x) = \sum_{k=0}^{n} a_k \varphi_k(x)$$

is recorded, namely: $p(x) = \alpha_0 + \alpha_1 x + \ldots + \alpha_n x^k$, then a function p(x) is a linear function with respect to a coefficient $\alpha_k$, and for a set of known discrete data points $(x_0, y_0)$, $(x_1, y_1)$, ..., and $(x_m, y_m)$, a set of $\alpha_k$ satisfying the following formula may be solved:

$$I = \sum_{i=0}^{m} [p(x_i) - y_i]^2,$$

Then a least square fitting function of this set of discrete data may be the function p(x), and to obtain a minimum I, conditions for an extreme value of a multivariate function may be obtained:

$$\sum_{k=0}^{n} \left( \sum_{i=0}^{m} \varphi_j(x_i) \varphi_k(x_i) \right) \cdot a_k = \sum_{i=0}^{m} \varphi_j(x_i) y_i, \quad j = 0, 1, \ldots, n,$$

and

Assuming that $$(\varphi_i, y) = \sum_{k=0}^{n} \varphi_i(x_k) y_k, \quad (\varphi_j, \varphi_k) = \sum_{i=0}^{m} \varphi_j(x_i) \varphi_k(x_i)$$

is recorded, then the above formula is transformed into:

$$\begin{bmatrix} n & \sum_{i=1}^{n} x_i & \cdots & \sum_{i=1}^{n} x_i^k \\ \sum_{i=1}^{n} x_i & \sum_{i=1}^{n} x_i^2 & \cdots & \sum_{i=1}^{n} x_i^{k+1} \\ \vdots & \vdots & \vdots & \vdots \\ \sum_{i=1}^{n} x_i^k & \sum_{i=1}^{n} x_i^{k+1} & \cdots & \sum_{i=1}^{n} x_i^{2k} \end{bmatrix} \begin{bmatrix} a_0 \\ a_1 \\ \vdots \\ a_n \end{bmatrix} = \begin{bmatrix} \sum_{i=1}^{n} y_i \\ \sum_{i=1}^{n} x_i y_i \\ \vdots \\ \sum_{i=1}^{n} x_i^k y_i \end{bmatrix},$$

Through conversion to a Vandermonde matrix, the following is obtained:

$$\begin{bmatrix} 1 & x_1 & \cdots & x_1^k \\ 1 & x_2 & \cdots & x_2^k \\ \vdots & \vdots & & \vdots \\ 1 & x_n & \cdots & x_n^k \end{bmatrix} \begin{bmatrix} a_0 \\ a_1 \\ \vdots \\ a_n \end{bmatrix} = \begin{bmatrix} y_1 \\ y_2 \\ \vdots \\ y_n \end{bmatrix},$$

The formula is expressed for short as:

$X \cdot A = Y$, and

By solving a coefficient matrix A, a fitting curve of the polynomial least squares method (PLSM) may be obtained.

Further, a specific method of Step 1.2 may be as follows:

Step 1.2.1, fitting an operation area to the closest polygon to obtain coordinates of each vertex of the polygon in the operation area;

Step 1.2.2, calculating a longest edge of the operation area according to coordinate information of the vertexes;

Step 1.2.3, constructing a route coordinate system: constructing a geodetic coordinate system and the route coordinate system based on the longest edge;

Step 1.2.4, performing coordinate system conversion: converting the coordinates of the vertexes from the geodetic coordinate system into the route coordinate system;

Step 1.2.5, performing route planning and task point coordinate acquisition: after the coordinate system is built, planning a route according to actual needs; and setting a distance between the routes and a distance between the task points, planning an UAV flight route parallel to the longest edge in the route coordinate system, and obtaining route coordinates of all the task points for data acquisition; and Step 1.2.6, constructing the task queue: starting from an origin, traversing all the task points along the route back and forth, converting the route coordinates of all the task points into geographic coordinates, and adding the geographic coordinates into the task queue successively.

Further, a specific method of step 1.4 may be as follows:

Step 1.4.1, reading geodetic coordinates of the next target point from the task queue, obtaining geodetic coordinates and Euler angle data of an initial position of the UAV from a flight control system, and converting the geodetic coordinates into a body coordinate system;

Step 1.4.2, after coordinate system conversion is completed, calculating expected moving distances $D_x$ and $D_y$ in X-axis and Y-axis respectively from coordinates of an initial point and the target point;

Step 1.4.3, setting an allowable error d and a step size s, where the allowable error d represents a maximum error allowed by the system, the UAV may be considered to reach the target point when distance errors between positions of the UAV and the target point in both X-axis and Y-axis directions are less than d, and the step size s represents a maximum displacement of the system to adjust movement of the UAV each time;

Step 1.4.4, obtaining the geodetic coordinates and Euler angle data of a current position of the UAV through the flight control system, and converting the geodetic coordinates into the body coordinate system;

Step 1.4.5, calculating moving distances dx and dy of the UAV in the X-axis and Y-axis directions through the current position of the UAV and the initial position of the UAV, and calculating distances to be moved of the UAV $dx_0$ and $dy_0$ according to the expected moving distances and the moving distances;

Step 1.4.6, determining whether the current position of the UAV has reached the target point within the allowable error of the system, if so, ending a control method and enabling the UAV to hover over the target point to wait for a command, and if not, proceeding to the next step; and Step 1.4.7, determining whether the distance to be moved is less than the step size s in the X-axis and Y-axis directions respectively, if so, controlling the UAV to move the remaining distance in this direction in the next step; and if not, controlling the UAV to move a distance s in this direction; and after the movement is completed, returning to step 1.4.4.

Further, step 1.5 may be specifically as follows:

Step 1.5.1, descending in a first stage: in the first stage, controlling the UAV to quickly descend to an altitude of $h_1$ according to the UAV's own GPS data and altitude data of a barometer;

Step 1.5.2, descending in a second stage: in the second stage, controlling the UAV to slowly descend to the altitude of $h_2$ based on altitude information of a current distance measurement sensor and the ground measured in real time by an altitude hold module of the system, where $h_2$ is the altitude of data acquisition operation of the system.

Further, a specific method of step 1.2.5 may be as follows:

Performing route planning and task point coordinate acquisition: after the coordinate system is built, planning the route according to actual needs; and setting the distance between the routes and the distance between the task points, planning the UAV flight route parallel to the longest edge in the route coordinate system, and obtaining the route coordinates of all the task points for data acquisition; and Calculating a largest y-axis coordinate $y_{max}=\max(y_{V1}, y_{V2}, \ldots, y_{Vn})$ among the m vertexes of the polygon fitted in step 1.2.1, setting a distance D between two adjacent routes, and drawing a set of straight lines with a distance of D and parallel to $y_{V1}y_{V2}$ between y=0 and y=$y_{max}$; in XOY coordinate plane, reserving the route inside the polygon by calculating an intersection of the polygon fitted in step 1.2.1 and the set of straight lines to obtain the final UAV operation route; and after planning the route, determining a distance d between two adjacent task points in a route, traversing each route, determining the number of task points for each route by a formula (3), and distributing these task points uniformly on the route:

$$n_i = rund\left(\frac{x_{i2} - x_{i1}}{d}\right) + 1,$$

In the formula, $n_i$ represents the number of task points on an i-th route, rund represents the rounding to the nearest integer, and $x_{i2}$ and $x_{i1}$ are X-axis coordinates of right and left endpoints of the route respectively.

Further, step 1.5.1 may be specifically as follows:

S1, reading information of $h_1$, $h_2$, allowable altitude error h, and allowable roll angle error r;

S2, obtaining geodetic coordinates and Euler angle data of a current position of the UAV, and converting the geodetic coordinates into a body coordinate system;

S3, calculating an expected displacement $Z_1=H-h_2$ through a current altitude of the UAV and $h_2$;

S4, obtaining, by the system, geodetic coordinates and Euler angle data of a current position of the UAV again, and converting the geodetic coordinates into the body coordinate system;

S5, reversely adjusting, by the system, a roll angle according to a current roll angle of the UAV;

S6, calculating and determining the remaining displacement $Z_2=h_{now}-h_2$ according to the current altitude of the UAV, where $h_{now}$ is the current altitude of the UAV;

S7, determining whether the remaining displacement is less than the allowable error h or a negative number, and if so, entering S10, otherwise entering step S8 and continuing execution;

S8, determining whether the remaining displacement is less than the set step size, and if so, descending the UAV by an altitude of z, otherwise descending the UAV by a maximum step size;

S9, recalculating the remaining displacement, and according to the different descending altitudes z being 0 or $Z_2-s$ in the previous step, performing step S8 again; and S10, determining whether an absolute value of the current roll angle is within a range of the allowable error of the system, and if so, completing the first stage for control and entering the second stage, otherwise performing step S4.

Further, step 1.5.2 may be specifically as follows:

D1, obtaining real-time altitude data, and determining whether an absolute value of a difference between altitude data and a working altitude meets the allowable error of the system, and if so, waiting for subsequent data acquisition, otherwise continuing execution; and D2, calculating a smaller value of 0.05 m and 0.7 times the absolute value of the difference between the altitude data and the working altitude, then controlling the UAV to move down a distance of this smaller value, and performing step D1 after completion.

The present disclosure researches and implements a special control and monitoring system for the UAV according to specific application scenarios using the embedded equipment, further expanding the practical application capability of the UAV. The present disclosure combines the UAV technology and the XRF technology, integrates hardware such as the embedded equipment, portable equipment, and a variety of sensors, as well as the electronic technology and the computer technology, and integrates multiple disciplines, which has important reference value for solving the difficulties encountered in other professional fields such as environmental monitoring. In view of the severe soil heavy metal pollution situation and practical application requirements, the present disclosure develops software and hardware system equipment for rapid detection of soil heavy metal pollution, which makes up for the deficiencies of the prior art and provides a new and complete solution for the difficulties faced in the practical application of detection of soil heavy metal pollution.

DETAILED DESCRIPTION OF THE EMBODIMENTS

In order to make the objectives, technical solutions and advantages of the present disclosure more clear, the present disclosure will be further described in detail below with reference to the implementation and drawings.

Figure 1:
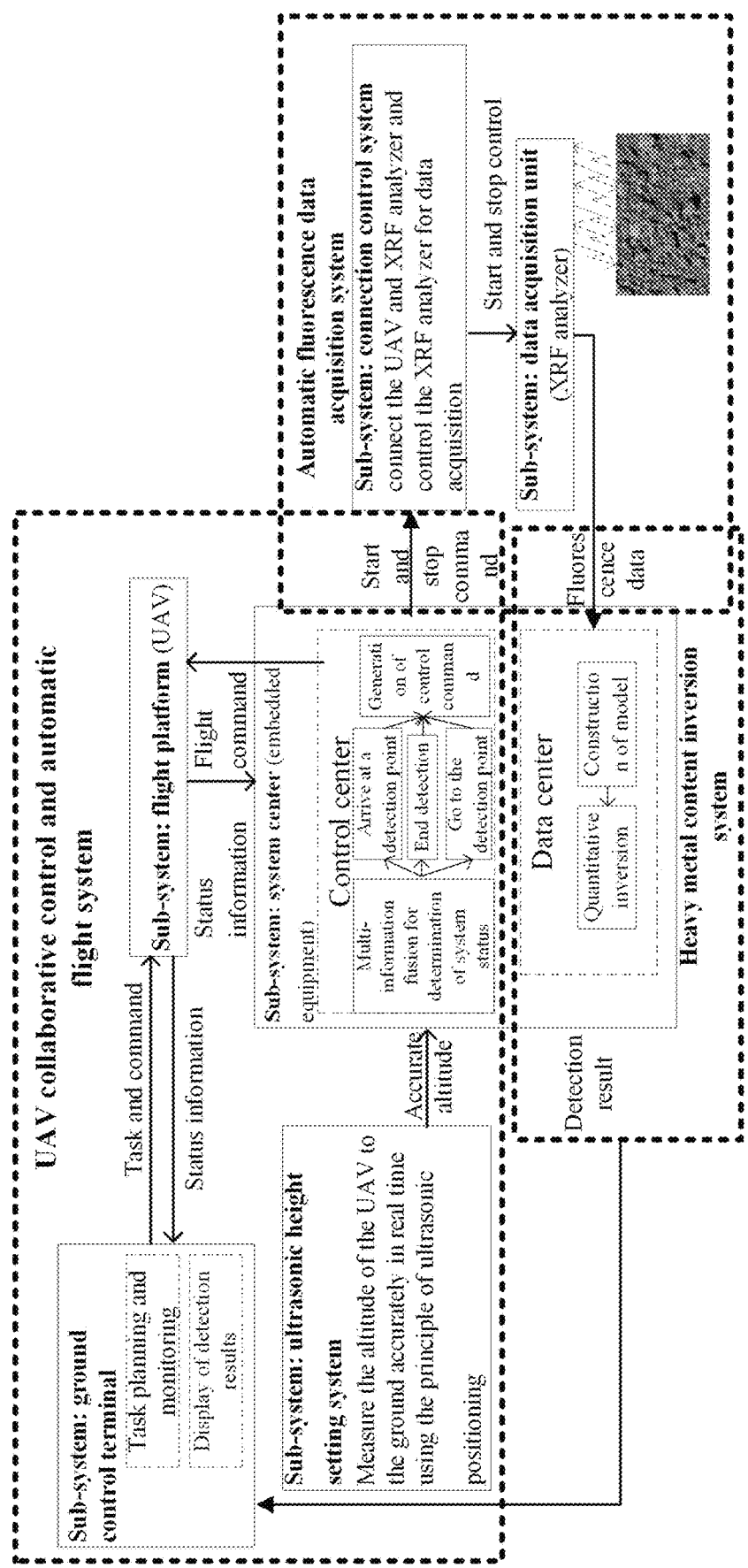
FIG. 1 is an overall technical roadmap of the present disclosure.

The present disclosure finally realizes a set of software-hardware coordinated UAV-borne XRF system for rapid detection of soil heavy metal pollution, which can realize the functions of flight task planning, automatic control of flight altitude and velocity, and real-time monitoring of the flight status of an UAV. A portable XRF analyzer can automatically and accurately detect the contents of heavy metals in soil at a certain distance, and the function of regional, rapid, and convenient detection of soil heavy metal pollution is realized, which provides a new solution for the difficulties faced in the practical application of detection of soil heavy metal pollution. An overall technical roadmap of the present disclosure is shown in FIG. 1.

According to the hardware, the technical roadmap can be mainly divided into five subsystems including a ground control terminal, a flight platform, a system center, a connection driver module, and a data acquisition unit.

(1) Ground control terminal: an interactive window between the user and the system. The user plans and submits tasks through equipment such as computers and monitors the flight status of the UAV in real time. The flight of the UAV can be controlled at any time through commands or the remote control of the UAV. On the one hand, it also receives the final detection result processed by the embedded equipment and displays it to the user.

(2) Flight platform: the UAV and its auxiliary connecting devices constitute the load and flight platform of the system. The flight control system of the UAV is mainly responsible for communication with the embedded equipment and portable equipment. According to the planned tasks, the control commands from the remote control of the UAV and the embedded equipment control the flight of the UAV.

(3) System center: the embedded equipment is the control and data processing center of the entire system. It mainly has two functions: one is the control center, which comprehensively determines the current state of the system according to the received information, and send timely and appropriate control commands to the XRF connection driver module and the UAV. The second is the data center, which receives the data acquired by XRF, performs necessary inversion of the data to obtain metal content information, and saves the detection results locally and sends them to the portable equipment for display.

(4) Connection driver module: it mainly connects the UAV platform with the portable XRF analyzer, and realizes the automatic drive of data acquisition of the XRF analyzer instead of human hands.

(5) Data acquisition unit: the portable XRF analyzer is the data acquisition unit of the system, which is controlled by a data acquisition driving device for data acquisition, and sends the acquired fluorescence data to the embedded equipment for further processing.

A complete task implementation process is as follows: The user inputs the coordinates of the task area, the system first plans the task route to build the task queue, the UAV flies over the first task point according to the task, and the control center determines when the UAV reaches the task point based on information such as the task point data and GPS data. Then the control center sends commands to control the UAV to descend, controls the UAV to hover when determining that the UAV descends to the specified altitude using real-time information such as the velocity, altitude, GPS data, and data of the altitude hold module of the UAV, and sends commands to control the XRF analyzer to acquire data at the same time. When the data acquisition is completed, the control center controls the UAV to rise to the altitude and fly to the next mission point, and the data center inverts the data at the same time. The above process is repeated until the entire task is completed and the UAV returns.

Figure 2:
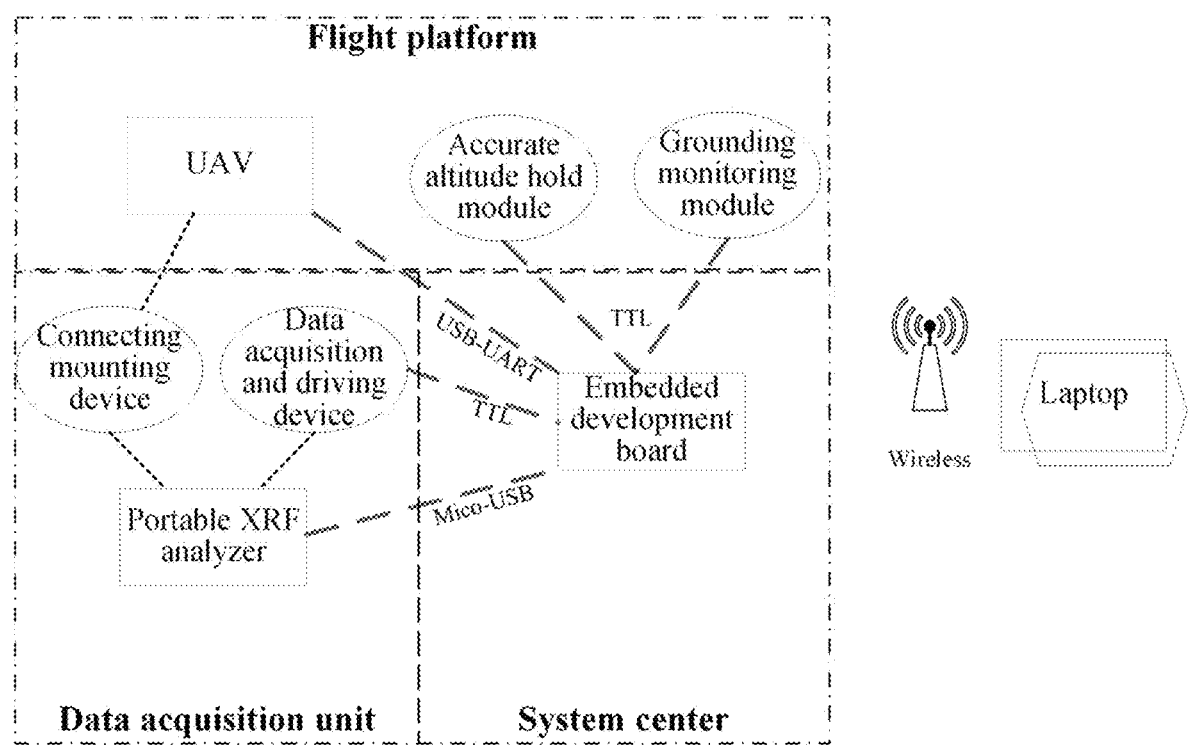
FIG. 2 is an overall hardware structure diagram of the present disclosure.

It can be seen from FIG. 2 that the hardware of the present disclosure can be divided into three parts as a whole according to different functions, namely the system center based on the embedded development board, the system flight platform based on the UAV, and the data acquisition unit based on the portable XRF analyzer. In the system, the UAV and the portable XRF analyzer are connected through a connecting device. The embedded development board communicates with the UAV through USB-UART (Universal Asynchronous Receiver/Transmitter), and obtains the accurate altitude information of the current UAV through the UART communication protocol and sends flight commands to the flight control system of the UAV, controls the data acquisition driving device to acquire data through transistor-transistor logic (TTL) signals, and also acquires the data of the accurate altitude hold module and the grounding monitoring module through the TTL signals. The portable XRF analyzer sends the acquired data to the embedded development board through the Micro-USB data line. The operator on the ground uses a laptop to communicate with the embedded development board through a wireless network to control the entire system.

It can be seen from FIG. 1 that the software of the present disclosure includes an UAV cooperative control and automatic flight system, an automatic XRF data acquisition system, and a heavy metal content inversion processing system.

UAV automatic flight control module: the operation route and task points are planned according to the detection area, on this basis, the UAV equipped with other hardware equipment is controlled to fly according to the predetermined route and trajectory, and through cooperation with other software and hardware modules, the data acquisition task is completed.

Sensor hardware data acquisition and analysis module: it has the functions of acquiring the data of the altitude hold module and acquiring and analyzing the data of the grounding monitoring module, and assists the automatic flight control module of the UAV to realize the accurate, stable and safe operation of the UAV.

Data acquisition and processing module: it is responsible for controlling the data acquisition driving device to realize the automatic control of the data acquisition process, as well as constructing the inversion model of heavy metal elements in the soil, and obtaining the accurate content of heavy metal elements in the soil according to the original data acquired by the system near the ground.

The three modules in the system software platform do not exist in isolation, and they are relatively independent but interconnected, and jointly realize the rapid detection of soil heavy metal pollution by UAV-borne XRF on the basis of the hardware platform.

Figure 3:
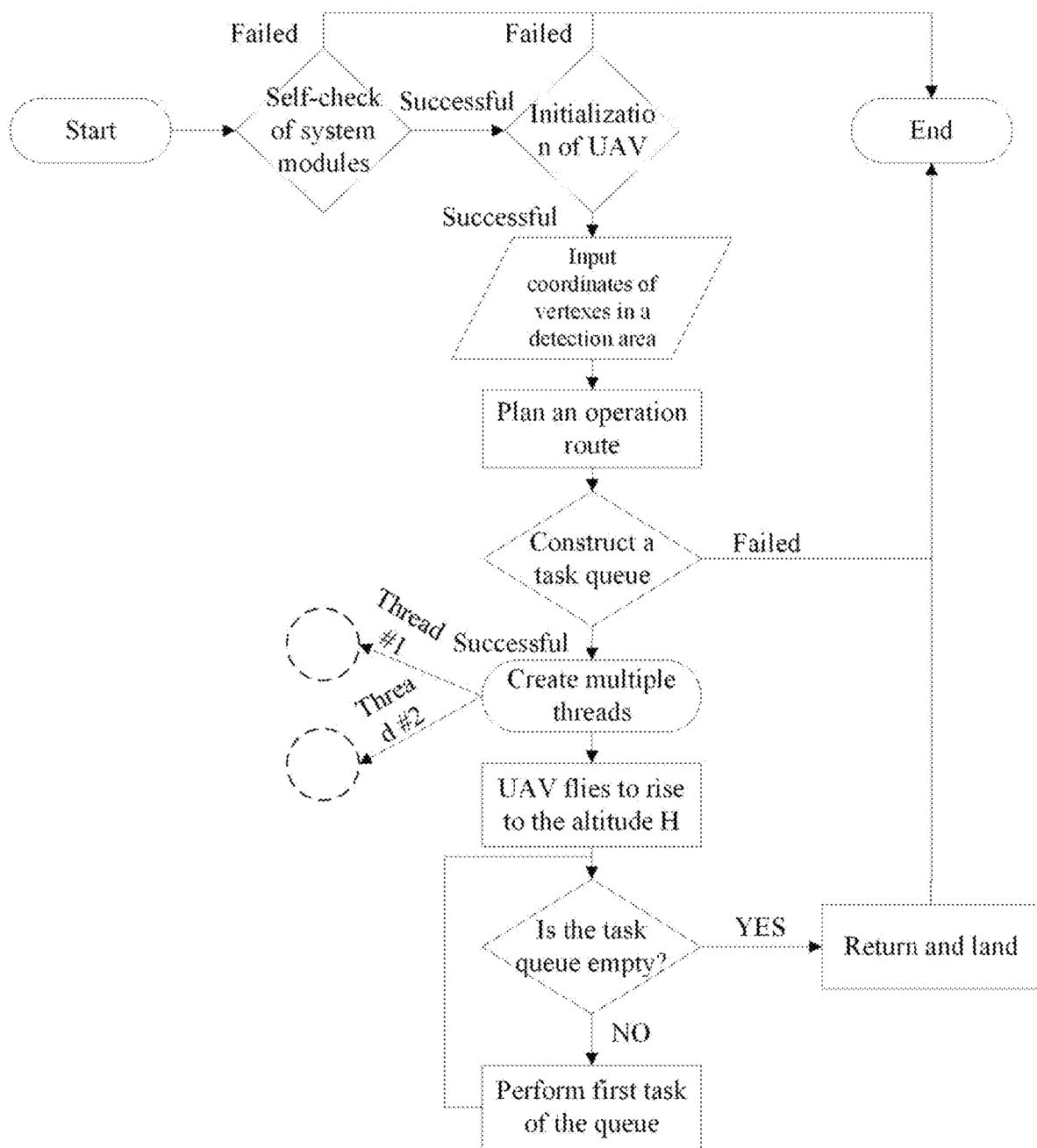
FIG. 3 is an overall flow chart of an UAV collaborative control and automatic flight system of the present disclosure.

The overall process of the UAV collaborative control and automatic flight system is shown in FIG. 3, including the following steps.

Step 1, each module of a system is initialized and self-checked to ensure that each module of the system works normally.

The system will first perform self-check on the development board and the UAV communication module, the altitude hold module, the grounding detection module, and the driving control device. The method will enter the next step when the software and hardware of these modules can work normally. Then the self-check program of the UAV will be started to ensure that the UAV can fly normally in the current state.

Step 2, an UAV flight task route for soil heavy metal pollution monitoring is planned, and a task queue is constructed. In order to minimize the number of times that the UAV changes the route direction during the operation, the system uses the method of planning the route parallel to the longest edge. The process is shown in FIG. 3. A specific process for processing is as follows.

Step 2.1, coordinates of each vertex of the polygon in an operation area are obtained.

Step 2.2, a longest edge of the polygon is searched, and the longest edge of the operation area is calculated according to coordinate information of the vertexes.

Step 2.3, a route coordinate system is constructed: a geodetic coordinate system and the route coordinate system are constructed based on the longest edge.

In a convex polygon with m vertexes, the longest edge is assumed to be $V_1V_2$ (the vertex $V_1$ is in the west of the vertex $V_2$). A geodetic coordinate system $X_nOY_n$ is established by taking the vertex $V_1$ as the origin and the due east and due north directions as $X_n$ and $Y_n$ axes, and the geodetic coordinate system is rotated around the origin by an angle $\theta$, such that $OX_n$ coincides with $V_1V_2$ to obtain a new route coordinate system XOY.

Step 2.4, coordinate system conversion is performed: the coordinates of the vertexes are converted from the geodetic coordinate system into the route coordinate system.

In a detection area, all the vertexes of the area are in the Eastern Hemisphere and the difference in latitude and longitude between them is very small, and the influence of the curvature of the earth can be ignored. A formula for converting the coordinates of the vertexes from the geodetic coordinate system into the route coordinate system is:

$$\binom{x}{y} = \left[\binom{xn}{yn} - \binom{xn_{A_1}}{yn_{A_1}}\right] \cdot \begin{pmatrix} \cos\theta & \sin\theta \\ -\sin\theta & \cos\theta \end{pmatrix} \cdot \begin{pmatrix} R_c \pi \cos\left(\frac{\pi yn_{A_1}}{180}\right) \\ \frac{180}{R_j \pi} \\ \frac{180}{180} \end{pmatrix}. \quad (1)$$

In the formula, x and y are the coordinates of the vertexes in the route coordinate system, in meters; xn and yn are the longitude and latitude in the geographic coordinates of the vertexes, in degrees; $R_c$ and $R_j$ are the equatorial radius and polar radius of the earth respectively, $R_c$=6378137 m, $R_j$=6356725 m; $\pi$ is 3.14159265; $\theta$ is the rotation angle of the coordinate system, which can be calculated by formula (2):

$$\theta = \arctan\left(\frac{(yn_{A_2} - yn_{A_1}) \cdot \frac{R_j \pi}{180}}{\frac{(xn_{A_2} - xn_{A_1})}{180} \cdot R_c \pi \cos\left(\frac{\pi yn_{A_1}}{180}\right)}\right). \quad (2)$$

Figure 4:
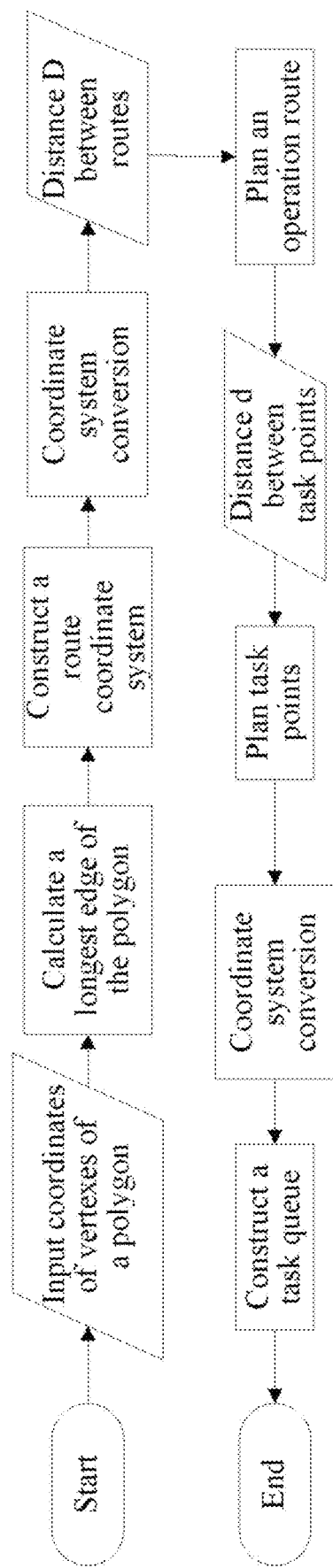
FIG. 4 is a flow chart of route planning and task queue construction of the present disclosure.

Step 2.5, route planning and task point coordinate acquisition are performed: after the coordinate system is built, a route is planned according to actual needs. A distance between the routes and a distance between the task points are set, an UAV flight route parallel to the longest edge is planned in the route coordinate system, and route coordinates of all the task points for data acquisition are obtained, as shown in FIG. 4.

A largest y-axis coordinate $y_{max}=\max(y_{V1}, y_{V2}, \ldots, y_{Vn})$ is calculated among the m vertexes. A parameter D is input to represent a distance between two adjacent routes, and a set of straight lines with a distance of D and parallel to $y_{V1}y_{V2}$ is drawn between y=0 and $y=y_{max}$. In XOY, any edge $A_iA_{i+1}$ of the polygon can be calculated, where i∈ (1, 2, ..., m−1). The route inside the polygon is reserved by calculating an intersection of these parallel lines and the edge of the polygon to obtain the final UAV operation route. After planning the route, a distance d is input to represent a distance between two adjacent task points in a route, each route is traversed, the number of task points for each route is determined by Formula (3), and these task points are distributed uniformly on the route:

$$n_i = rund\left(\frac{x_{i2} - x_{i1}}{d}\right) + 1. \tag{3}$$

In the formula, n, represents the number of task points on an i-th route, rund represents the rounding to the nearest integer, and $x_{i2}$ and $x_{i1}$ are X-axis coordinates of right and left endpoints of the route respectively.

Step 2.6, the task queue is constructed: starting from an origin, all the task points are traversed along the route back and forth, the route coordinates of all the task points are converted into geographic coordinates, and added into the task queue successively to obtain the job task queue under the control of parameters D and l. Formula (4) is a method for converting the coordinates of the task points into geographic coordinates.

$$\begin{pmatrix} xn \\ yn \end{pmatrix} = \begin{pmatrix} x \\ y \end{pmatrix} \cdot \begin{pmatrix} \cos\theta & -\sin\theta \\ \sin\theta & \cos\theta \end{pmatrix} \cdot \begin{pmatrix} \dfrac{180}{R_c\pi\cos\left(\dfrac{\pi y n_{A_1}}{180}\right)} \\ \dfrac{180}{R_j\pi} \end{pmatrix} + \begin{pmatrix} xn_{A_1} \\ yn_{A_1} \end{pmatrix}. \tag{4}$$

Step 3, the UAV takes off: when the task queue is valid, the UAV takes off to a specified altitude H, where H is the set plane flight altitude of the UAV.

Figure 5:
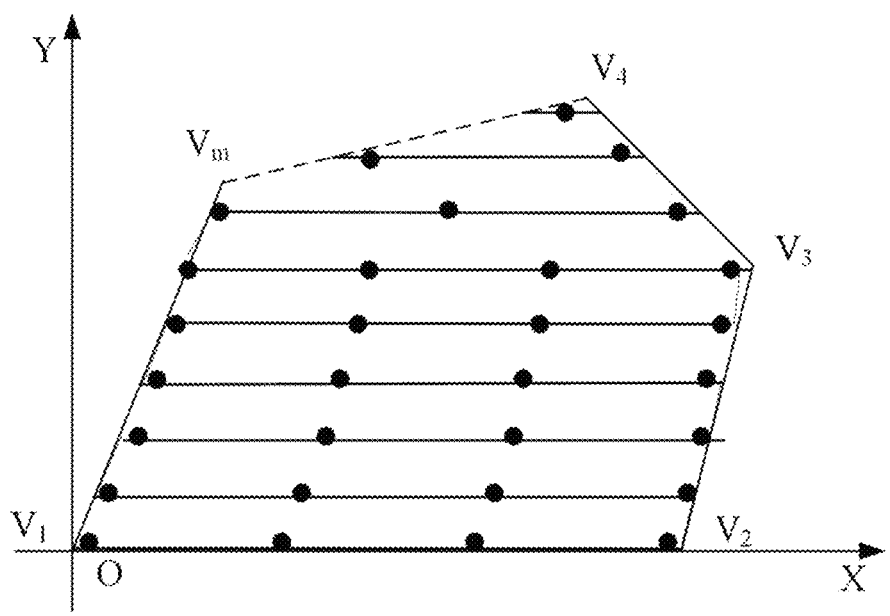
FIG. 5 is a schematic diagram of routes and task points of the present disclosure.

Step 4, automatic control of plane flight of the UAV is performed: the UAV is controlled to fly over the next task point. A flight path of an operation plane of the UAV is a straight line from a point A to a point B, and the altitude remains unchanged at the flight altitude H. During the plane flight of the UAV, the altitude control is not considered, and it is mainly aimed at controlling the movement of the UAV in the X-axis and Y-axis in the body coordinate system. A control algorithm for plane flight of the UAV is shown in FIG. 5, and a specific process is as follows.

Step 4.1, geodetic coordinates of the next target point is read from the task queue, geodetic coordinates and Euler angle data of an initial position of the UAV are obtained from a flight control system, and the geodetic coordinates are converted into a body coordinate system.

Step 4.2, after coordinate system conversion is completed, expected moving distances Dx and Dy in X-axis and Y-axis are calculated respectively from coordinates of an initial point and the target point.

Step 4.3, the system reads a preset allowable error d and step size s. The allowable error d represents a maximum error allowed by the system, the UAV is considered to reach the target point when distance errors between positions of the UAV and the target point in both X-axis and Y-axis directions are less than d, and the step size s represents a maximum displacement of the system to adjust movement of the UAV each time.

Step 4.4, the system obtains the geodetic coordinates and Euler angle data of a current position of the UAV through the flight control system, and converts the geodetic coordinates into the body coordinate system.

Step 4.5, moving distances dx and dy of the UAV in the X-axis and Y-axis directions are calculated through the current position of the UAV and the initial position of the UAV, and distances to be moved of the UAV $dx_0$ and $dy_0$ are calculated through Formula (5).

$$\begin{cases} dx_0 = Dx - dx \\ dy_0 = Dy - dy \end{cases}. \tag{5}$$

Step 4.6, whether the current position of the UAV has reached the target point within the allowable error of the system is determined, if so, the control algorithm ends and the UAV hovers over the target point to wait for a command, and if not, the algorithm proceeds to the next step.

Step 4.7, whether the distance to be moved is less than the step size s in the X-axis and Y-axis directions respectively is determined, if so, the UAV is controlled to move the remaining distance in this direction in the next step, and if not, the UAV is controlled to move a distance s in this direction. After the movement is completed, the algorithm returns to step 4.4.

Figure 6:
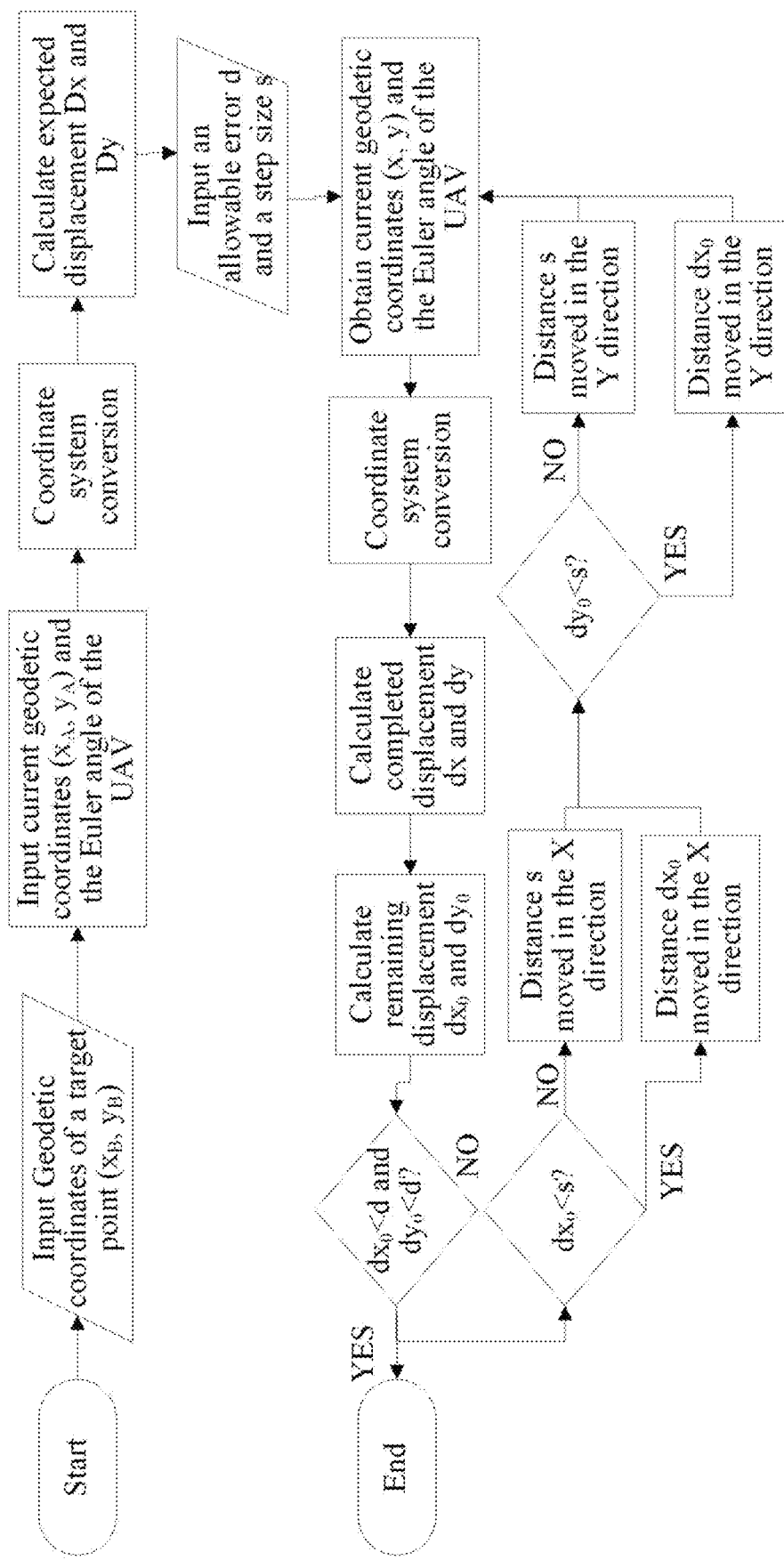
FIG. 6 is a flow chart of a control algorithm for plane flight of an UAV of the present disclosure.
Figure 7:
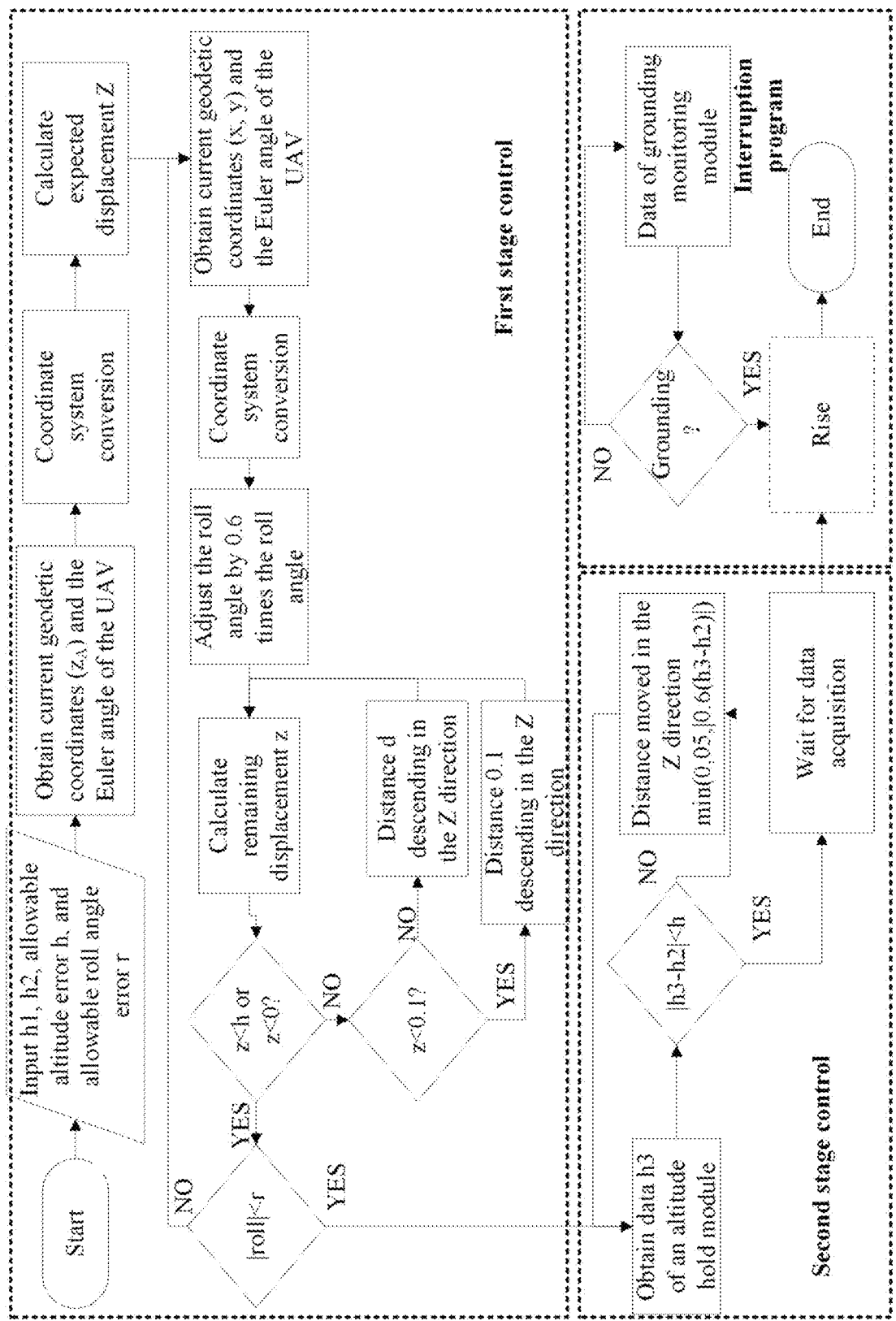
FIG. 7 is a flow chart of a control algorithm for a descending process of the UAV of the present disclosure.

Step 5, automatic control of a descending process of the UAV is performed: in order to acquire valid data, the UAV is controlled to descend to a predetermined altitude and hover for completion of data acquisition. The UAV descends in two stages. A control algorithm for a descending process of the UAV is shown in FIG. 6, and a specific process is as follows.

Step 5.1, descending in a first stage: in the first stage, the UAV is controlled to quickly descend to an altitude of $h_1$ according to the UAV's own GPS data and altitude data of a barometer.

In the first stage, the UAV descends from the flight altitude H to the altitude $h_1$, and $h_1$ is selected from 1-2 m according to the actual situation. In this stage, the UAV is not easily affected by ground objects and personnel, and the system is relatively safe as a whole. Therefore, in this stage, the descending control of the UAV is mainly realized with the aid of the UAV's own GPS data. At the same time, in order to ensure that the probe of the portable XRF analyzer is vertical to the ground during data acquisition, the roll angle of the aircraft is also controlled at this stage. A specific process is as follows.

Step 5.1.1, the system reads information of $h_1$, $h_2$, allowable altitude error h, and allowable roll angle error r.

Step 5.1.2, the system obtains geodetic coordinates and Euler angle data of a current position of the UAV through the flight control system, and converts the geodetic coordinates into a body coordinate system.

Step 5.1.3, an expected displacement $Z_1 = H - h_2$ is calculated through a current altitude of the UAV and $h_2$.

Step 5.1.4, the system obtains geodetic coordinates and Euler angle data of a current position of the UAV through the flight control system again, and converts the geodetic coordinates into the body coordinate system.

Step 5.1.5, the system reversely adjusts the current roll angle of the UAV with a value 0.6 times.

Step 5.1.6, the remaining displacement $Z_2=h_{now}-h_2$ is calculated and determined according to the current altitude of the UAV $h_{now}$ is the current altitude of the UAV.

Step 5.1.7, whether the remaining displacement is less than the allowable error h or a negative number is determined, and if so, the algorithm enters S10, otherwise enters step 5.1.8 and execution is continued.

Step 5.1.8, whether the remaining displacement is less than 0.1 m is determined, and if so, the UAV descends by an altitude of z, otherwise descends by a maximum step size 0.1 m.

Step 5.1.9, the remaining displacement is recalculated, and according to the different descending altitudes z being 0 or $Z_2$–0.1 in the previous step, step 5.1.8 is performed again.

Step 5.1.10, whether an absolute value of the current roll angle is within a range of the allowable error of the system is determined, and if so, the first stage for control is completed and the algorithm enters the second stage, otherwise step 5.1.4 is performed.

Step 5.2, descending in a second stage: in the second stage, the UAV is controlled to slowly descend to the altitude of $h_2$ based on altitude information of a current distance measurement sensor and the ground measured in real time by an altitude hold module of the system, where $h_2$ is the altitude of data acquisition operation of the system. The second stage of the descending process of the UAV is an important step to realize data acquisition. The UAV control in this stage maintains safe and prudent. A specific process is as follows.

Step 5.2.1, data of the altitude hold module is obtained, whether an absolute value of a difference between the data of the altitude hold module and a working altitude meets the allowable error of the system is determined, and if so, subsequent data acquisition is waited, otherwise execution is continued.

Step 5.2.2, a smaller value of 0.05 m and 0.7 times the absolute value of the difference between the data of the constant altitude module and the working altitude is calculated, then the UAV is controlled to move down a distance of this smaller value, and step 5.2.1 is performed after completion.

Step 6, the UAV hovers and data acquisition is performed: the UAV keeps hovering at an altitude of $h_2$ accurately until the data acquisition is completed. Step 4 is repeated until the data acquisition is completed for all task points in the task queue.

Step 7, the UAV returns and lands: the UAV is automatically controlled to return to coordinates of a take-off point and land.

Automatic XRF data acquisition system:

When the portable XRF analyzer acquires data, the trigger of the fuselage needs to be pulled to start the data acquisition function. Therefore, in order to realize the function of automatic data acquisition, the present disclosure designs and realizes a data acquisition driving device instead of manually pulling the trigger. Under the control of the control signal of the development board, the driving structure of the driving device can simulate the human hand to control the trigger of the portable XRF analyzer. A specific process includes the following steps.

Step 1, the embedded equipment general purpose input/output ports (GPIO) environment is initialized.

Since the GPIO pins need to be used for IO communication, the GPIO pins of the Raspberry Pi need to be initialized.

Step 2, the pin mode is defined.

According to the circuit connection diagram, the corresponding pin numbers are defined and all set to output mode.

Step 3, the embedded equipment outputs a control signal and starts data acquisition.

For a DC electromagnet, when the signal IN is at high level, the electromagnet is energized and the trigger is pulled, otherwise the trigger is released. For an electric push rod, when the EN, IN1, and IN2 signals are all at high level, the push rod is extended and the trigger is released, when only IN1 is at low level, the push rod is retracted, the trigger is pulled, and when all three signals are at low level, the push rod is stationary.

Step 4, data acquisition is performed, the portable XRF analyzer starts to acquire data and record and store data such as the type and content of heavy metal elements in the soil at this point.

Heavy metal content inversion processing system:

The system for rapid detection of soil heavy metal pollution by UAV-borne XRF is limited by the complex environment on the ground. In order to ensure the safety of the system, the portable XRF analyzer cannot perform detection on the ground during data acquisition, but adopts the method of near-ground detection. The increase in the distance leads to a decrease in the amount of acquired X-fluorescence. Therefore, the calibration curve constructed by the portable XRF analyzer's own data processing system for ground detection is invalid. The system needs to rebuild a suitable model curve to invert the content data of heavy metal elements obtained by the near-ground detection into the content data of heavy metal elements measured in the ground detection. Based on linear least square fitting, the present disclosure obtains a linear fitting function from near-ground detection data to ground detection data, and realizes data inversion through the fitting function. This process includes the following steps.

Step 1, data acquisition is performed. Enough sampling points are uniformly selected in an area to be detected, and each sampling point is detected respectively near the ground and on the ground to obtain content data of a set of metal elements to be detected.

Step 2, data check and data preprocessing are performed. After data acquisition is completed, a scatter plot is drawn from known data for data check, obviously wrong data is eliminated, and a fitting degree m of a polynomial is preliminarily determined according to a preliminary image.

Step 3, polynomial fitting functions with highest degrees of m−1 and m and the sum of squared errors err are calculated successively.

Further, it is assumed that there are n+1 linearly independent continuous functions.

$\varphi_0(x), \varphi_1(x), \ldots, \varphi_n(x)$, where $\varphi_k(x)=x^k$, k=1, 2, ..., n, $$p(x) = \sum_{k=0}^{n} a_k \varphi_k(x)$$

is recorded, namely: $p(x)=\alpha_0+\alpha_1 x+ \ldots +\alpha_n x^k$, k=1, 2, ..., n, then a function p(x) is a linear function with respect to a coefficient $\alpha_k$ (k=0, 1, ..., n), and for a set of known discrete data points $(x_0, y_0), (x_1, y_1), \ldots,$ and $(x_m, y_m)$, a set of $a_k$ (k=0, 1, ..., n) satisfying Formula (6) is solved, then a least square fitting function of this set of discrete data is the function p(x).

$$I = \sum_{i=0}^{m} [p(x_i) - y_i]^2 = \min. \tag{6}$$

To obtain a minimum value of the multivariate function (Formula (6)), conditions for an extreme value of the multivariate function are obtained:

$$\sum_{k=0}^{n} \left( \sum_{i=0}^{m} \varphi_j(x_i)\varphi_k(x_i) \right) \cdot a_k = \sum_{i=0}^{m} \varphi_j(x_i)y_i, \; j = 0, 1, \ldots, n. \tag{7}$$

Formula (7) is a system of linear equations about $\alpha_k$ (k=0, 1, ..., n), and it is assumed that $$(\varphi_i, y) = \sum_{k=0}^{m} \varphi_i(x_k)y_k, \; (\varphi_j, \varphi_k) = \sum_{i=0}^{m} \varphi_j(x_i)\varphi_k(x_i)$$

is recorded, then Formula (7) can be transformed into:

$$\begin{bmatrix} n & \sum_{i=1}^{n} x_i & \cdots & \sum_{i=1}^{n} x_i^k \\ \sum_{i=1}^{n} x_i & \sum_{i=1}^{n} x_i^2 & \cdots & \sum_{i=1}^{n} x_i^{k+1} \\ \vdots & \vdots & \vdots & \vdots \\ \sum_{i=1}^{n} x_i^k & \sum_{i=1}^{n} x_i^{k+1} & \cdots & \sum_{i=1}^{n} x_i^{2k} \end{bmatrix} \begin{bmatrix} a_0 \\ a_1 \\ \vdots \\ a_n \end{bmatrix} = \begin{bmatrix} \sum_{i=1}^{n} y_i \\ \sum_{i=1}^{n} x_i y_i \\ \vdots \\ \sum_{i=1}^{n} x_i^k y_i \end{bmatrix}. \tag{8}$$

Formula (8) can be converted into a Vandermonde matrix to obtain:

$$\begin{bmatrix} 1 & x_1 & \cdots & x_1^k \\ 1 & x_2 & \cdots & x_2^k \\ \vdots & \vdots & & \vdots \\ 1 & x_n & \cdots & x_n^k \end{bmatrix} \begin{bmatrix} a_0 \\ a_1 \\ \vdots \\ a_n \end{bmatrix} = \begin{bmatrix} y_1 \\ y_2 \\ \vdots \\ y_n \end{bmatrix}. \tag{9}$$

Formula (9) is expressed for short as:

$$X \cdot A = Y \tag{10}.$$

By solving a coefficient matrix A, a fitting curve of the PLSM is obtained.

Step 4, if a reduction amount of the sum of squared errors of the last fitting function compared with the sum of squared errors of the previous fitting function is greater than 10%, the fitting function with a highest order greater than m continues to be calculated successively until a reduction amount of the final sum of squared errors compared with the sum of squared errors of the previous fitting function is less than 10%.

Step 5, a fitting function corresponding to a minimum sum of squared errors is recorded and saved as a final inversion model.

Step 6, data inversion processing is performed. The data acquired by the system near the ground is inverted according to the inversion model to obtain accurate content data of heavy metal elements in soil, and the inverted data is recorded and saved.

Figure 8:
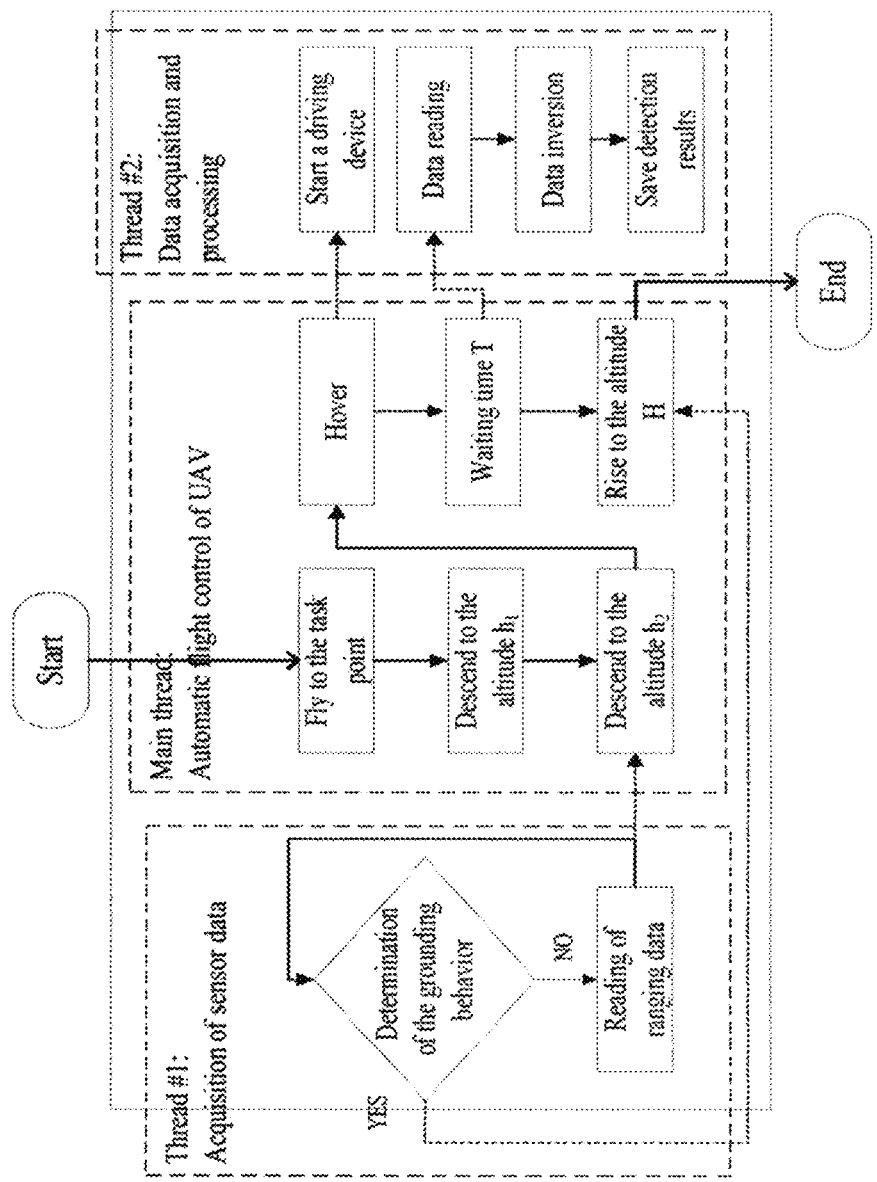
FIG. 8 is a schematic diagram of a data acquisition process of the present disclosure.
Figure 9:
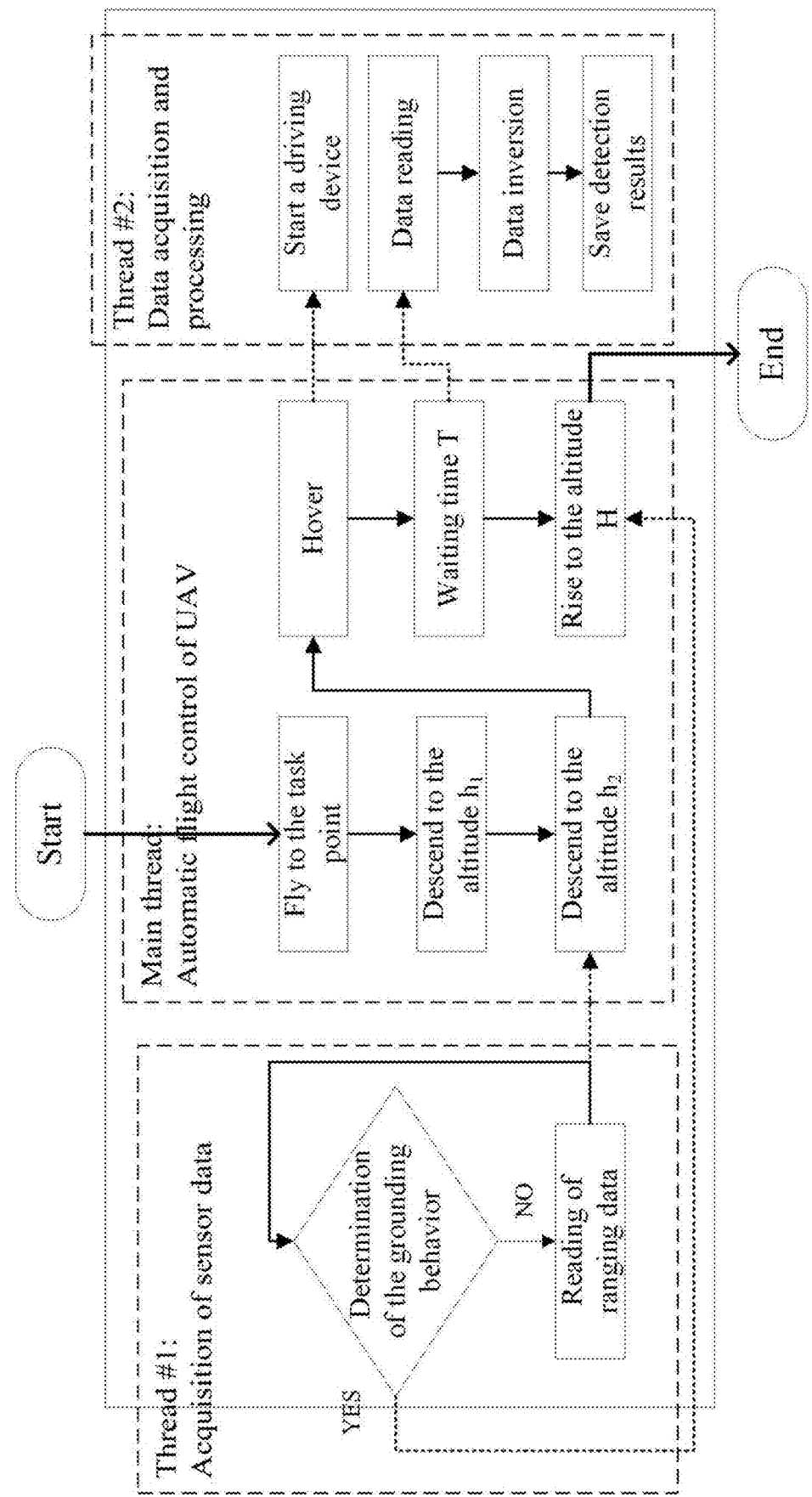

The three modules in the system software platform do not exist in isolation, and they are relatively independent but interconnected, and jointly realize the rapid detection of soil heavy metal pollution by UAV-borne XRF on the basis of the hardware platform. The present disclosure adopts a multi-threaded programming model, and uses one thread to execute the main task of a software module, and the three modules in the system software platform of different threads cooperate to complete a specific data acquisition task. A data acquisition process is shown in FIG. 8.

In the process of a data acquisition task, thread #1 will read the data of the grounding monitoring module and the ranging data of the altitude hold module cyclically at a frequency of 10 Hz, and determine whether the grounding behavior occurs. When the grounding behavior occurs, it will immediately control the UAV to fly to an altitude of H, ending the data acquisition task. Thread #1 will terminate after the UAV returns and lands.

During normal acquisition, the main thread controls the UAV to fly over the task point, and then start to descend. The UAV descends in two stages. In the first stage, the UAV is controlled to quickly descend to the altitude of $h_1$ according to the UAV's own GPS data and altitude data of a barometer. In the second stage, the UAV is controlled to slowly descend to the altitude of $h_2$ based on altitude information of a current distance measurement sensor and the ground measured in real time by the altitude hold module, where $h_2$ is the altitude of data acquisition operation of the system. After the UAV reaches the altitude for acquisition, it hovers and informs thread #2 to start the driving device, waits for a time T required to acquire data, then informs thread #2 to read and process the data again, and controls the UAV to rise to the flight altitude H and ends the current data collection task. The main thread will wait for the other two threads to finish normally before terminating.

Thread #2 starts the driving device under the signal control of the main thread to start data acquisition. After the data acquisition is completed, the data acquired this time is read and data inversion processing is performed to obtain the more accurate content of heavy metal elements in the soil at the current task point, and the original data and processed data are saved to the results file. Thread #2 terminates after all data is processed.

The present disclosure tests the practicability and effectiveness of the whole system through experiments, and the results show that the system realized herein can well complete the rapid detection of soil heavy metal pollution in a large area, which can greatly reduce labor and time costs. All software runs on the Raspberry Pi 4B development board. The hardware parameters of the development board and the main software environment configuration required by the system are shown in Table 1.

TABLE 1

Hardware parameters and system software environment configuration table

| Category | Item | Parameter/version |
|---|---|---|
| Hardware | CPU | 64 bit-core ARM cortex-72, 1.5 Ghz |
| | GPU | Videocore VI, 500 MHz |
| | RAM | 4 GB of LPDDR4 |
| | Network | Gigabit Ethernet, dual-band 802.11ac |
| | External interface | USB 2.0 interface*2, USB 3.0 interface*2 |
| | Memory | MicroSD, 128 GB |

TABLE 1-continued

Hardware parameters and system software environment configuration table

| Category | Item | Parameter/version |
|---|---|---|
| Software | OS | Raspbian GNU/Linux 10 (buster) |
| | DJI OSDK | >=3.9 |
| | CMake | >=3.13.4 |
| | GCC | >=8.3.0 |
| | python | >=3.7.3 |

The data sampling points are selected uniformly and randomly in the experimental area and the surrounding area, and a total of 83 groups of data of the sampling points are acquired. Through preliminary analysis, it is found that there are mainly a variety of metal elements in the detection area. In this experiment, the Ti element with higher overall content and the Zn element with lower overall content are selected as the inversion object to construct the inversion model. According to the X value from small to large, 83 groups of data are sorted and numbered successively, and then 14 groups of data such as the 3rd, 9th, . . . , and 81st groups of the two element content data are selected by equal spacing as the test data of the model accuracy. The other 69 groups of data are used as fitting data. The highest fitting degree is set to 5, and the fitting program in the system performs fitting experiments with the highest degree of 2 to 5 for 69 groups of data.

The sum of squared errors and standard deviation statistics of the four fitting functions of the Zn element are shown in Table 2. It can be seen from Table 2 that with the increase of the highest degree, the sum of squared errors and standard deviation of the fitting results decrease in turn, but the fitting error of the 5th degree polynomial is already very low, which is less than 5% lower than the 4th degree fitting result. In order to reduce the calculation, the 5th degree polynomial fitting function can be directly selected as the inversion model. The predicted value can be obtained by substituting the X value of the test data of the Zn element into the model. The true value and inversion results of the test data of the model are shown in Table 3.

TABLE 2

Sum of squared errors and standard deviation of Zn element fitting

| Highest degree | Sum of squared errors | Standard deviation (ppm) |
|---|---|---|
| 2 | 7665.28 | 10.54 |
| 3 | 7202.38 | 10.22 |
| 4 | 6391.23 | 9.62 |
| 5 | 6121.11 | 9.42 |

TABLE 3

Comparison of inversion results of content of Zn element

| True value | Inversion result | Error | Error percentage (%) |
|---|---|---|---|
| 39 | 36.85 | −2.15 | 5.51 |
| 61 | 62.41 | 1.41 | 2.31 |
| 82 | 86.27 | 4.27 | 5.21 |
| 106 | 100.43 | −5.57 | 5.25 |
| 117 | 112.86 | −4.14 | 3.54 |
| 131 | 126.73 | −4.27 | 3.26 |
| 143 | 147.44 | 4.44 | 3.10 |
| 205 | 213.22 | 8.22 | 4.01 |
| 259 | 247.44 | −11.56 | 4.46 |
| 268 | 284.1 | 16.10 | 6.01 |

TABLE 3-continued

Comparison of inversion results of content of Zn element

| True value | Inversion result | Error | Error percentage (%) |
|---|---|---|---|
| 304 | 287.97 | −16.03 | 5.27 |
| 349 | 324.01 | −24.99 | 7.16 |
| 335 | 354.02 | 19.02 | 5.68 |
| 382 | 418.22 | 36.22 | 9.48 |

It can be seen from the inversion results that the overall inversion accuracy is high, reaching more than 94%, which can well invert the content of the Zn element from the near-ground detection results to the accurate content value of the ground detection.

The sum of squared errors and standard deviation statistics of the fitting function of the Ti element are shown in Table 4. It can be seen from Table 4 that with the increase of the highest degree, the sum of squared errors and standard deviation of the first four fitting results decrease in turn. Therefore, it is necessary to continue to do higher degree polynomial fitting to find a better fitting function, and finally select the 8th degree polynomial fitting function as the inversion model. The predicted value can be obtained by substituting the X value of the test data of the Ti element into the model. The true value and inversion results of the test data of the model are shown in Table 5.

TABLE 4

Sum of squared errors and standard deviation of Ti element fitting

| Highest degree | Sum of squared errors ($\times 10^3$) | Standard deviation (ppm) |
|---|---|---|
| 2 | 49309 | 845.35 |
| 3 | 44974 | 807.34 |
| 4 | 40491 | 766.05 |
| 5 | 36402 | 726.34 |
| 6 | 32296 | 684.15 |
| 7 | 28774 | 645.77 |
| 8 | 27607 | 632.54 |

TABLE 5

Comparison of inversion results of content of Ti element

| True value | Inversion result | Error | Error percentage (%) |
|---|---|---|---|
| 7107 | 7504.16 | 397.16 | 5.59 |
| 9227 | 8817.78 | −409.22 | 4.44 |
| 10499 | 11078.56 | 579.56 | 5.52 |
| 11581 | 12025.57 | 444.57 | 3.84 |
| 12393 | 12921.97 | 528.97 | 4.27 |
| 16125 | 14502.59 | −1622.41 | 10.06 |
| 17283 | 15281.93 | −2001.07 | 11.58 |
| 18138 | 19005.94 | 867.94 | 4.79 |
| 20227 | 21898.14 | 1671.14 | 8.26 |
| 20744 | 21902.73 | 1158.73 | 5.59 |
| 24186 | 23438.04 | −747.96 | 3.09 |
| 26123 | 25004.02 | −1118.98 | 4.28 |
| 28681 | 30172.61 | 1491.61 | 5.20 |
| 32003 | 34014.57 | 2011.57 | 6.28 |

Table 5 shows that the method realized by the present disclosure can realize the inversion of the content of the Ti element, except that the inversion accuracy is greatly reduced when the content of the Ti element is about 15,000 ppm, the overall inversion accuracy can reach 93%.

The inversion model construction and model analysis and evaluation are performed on the two elements with large differences in overall content, Zn and Ti, in the experimental area. The results show that the inversion method realized by the present disclosure can realize the accurate inversion of different contents of metal elements in the soil.

After the inversion model is constructed, the system for rapid detection of soil heavy metal pollution by UAV-borne XRF realized by the present disclosure is used to detect the content of heavy metals in the soil in the experimental area. First, information such as the coordinates of the vertex of the experimental area and route parameters is input into the system, the system will complete the route planning and task queue construction, and then the UAV will perform the data acquisition and flight task, and cooperate with other software and hardware modules to complete the data acquisition. The system acquires data at 13 task points successively, and then inverts the data according to the constructed model. The detection values and inversion results of the Zn and Ti elements are shown in Table 6.

TABLE 6

Detection and inversion results of heavy metal elements in the experimental area

| Serial number | Content of Zn element (ppm) | | Content of Ti element (ppm) | |
|---|---|---|---|---|
| | Detection value | Inversion result | Detection value | Inversion result |
| 1 | 100 | 169.01 | 4337 | 7983.63 |
| 2 | 156 | 263.68 | 5729 | 10341.27 |
| 3 | 54 | 95.77 | 10390 | 14048.85 |
| 4 | 86 | 145.82 | 10480 | 14143.12 |
| 5 | 46 | 83.04 | 9308 | 13063.32 |
| 6 | 50 | 89.47 | 7422 | 11872.68 |
| 7 | 114 | 193.05 | 3708 | 6974.02 |
| 8 | 205 | 325.01 | 4568 | 8413.24 |
| 9 | 291 | 517.76 | 6897 | 11523.13 |
| 10 | 217 | 336.8 | 7147 | 11698.16 |
| 11 | 204 | 324.01 | 12488 | 16524.81 |
| 12 | 51 | 91.05 | 11680 | 15528.25 |
| 13 | 84 | 142.58 | 6402 | 11108.27 |

The practicability and effectiveness of the system realized by the present disclosure are tested by the rapid detection experiment of soil heavy metal pollution. The results show that the system can complete well the rapid detection of soil heavy metal pollution in a large area, which greatly reduces labor and time costs. The most time-consuming and labor-consuming process in the entire detection process is the construction of the inversion model, but the constructed model is not only for a small area of soil. Through reasonable selection of sampling points, unless the soil organic matter in the detection area greatly changes, otherwise, the inversion model can be constructed at one time for rapid detection and repeated use.

What is claimed is:

1. A method for detection of soil heavy metal pollution using an unmanned aerial vehicle (UAV) and an X-ray fluorescence (XRF) technology, comprising the following steps:

Step 1, uniformly selecting enough sampling points in an area to be detected using an XRF analyzer, and detecting each sampling point respectively near ground and on the ground to obtain content data of a set of metal elements to be detected;

Step 2, performing data check and data preprocessing, wherein after data acquisition is completed, a scatter plot is drawn from known data for data check, wrong data is eliminated, and a fitting degree n of a polynomial (or similar model) is determined according to preliminary data;

Step 3, calculating polynomial fitting functions with highest degrees of n−1 and n and a sum of squared errors successively;

Step 4, if a reduction amount of the sum of squared errors of a last fitting function compared with the sum of squared errors of a previous fitting function is greater than a set threshold, continuing to calculate the fitting function with a highest order greater than n successively until a reduction amount of a final sum of squared errors compared with the sum of squared errors of the previous fitting function is less than a set threshold;

Step 5, recording and saving a fitting function corresponding to a minimum sum of squared errors as a final inversion model; and Step 6, controlling the UAV to hover at an altitude of $h_2$ accurately acquiring, by the XRF analyzer carried on the UAV, soil data near the ground, and detecting, by the XRF analyzer accurate content data of heavy metal elements in soil by performing inversion on the soil data based on the final inversion model, wherein $h_2$ is the altitude for acquiring the soul data near the ground.

2. The method for detection of soil heavy metal pollution using an UAV and an XRF technology according to claim 1, wherein in step 6, a method for controlling the UAV when the XRF analyzer carried on the UAV acquires the soil data is as follows:

Step 1.1, initializing and self-checking each module of a system to ensure that each module of the system works normally;

Step 1.2, planning an UAV flight task route for soil heavy metal pollution monitoring, and constructing a task queue;

Step 1.3, enabling the UAV to take off: when the task queue is valid, enabling the UAV to take off to a specified altitude H, wherein H is the set plane flight altitude of the UAV;

Step 1.4, performing automatic control of plane flight of the UAV: controlling the UAV to fly over a next task point, wherein a flight path of an operation plane of the UAV is a straight line from a point A to a point B, and the altitude remains unchanged at the flight altitude H;

Step 1.5, performing automatic control of a descending process of the UAV: in order to acquire valid data, controlling the UAV to descend to a predetermined altitude and hover for completion of data acquisition;

Step 1.6, enabling the UAV to hover and performing data acquisition: keeping the UAV hovering at the altitude of $h_2$ accurately until the data acquisition is completed, and repeating step 1.4 until the data acquisition is completed for all task points in the task queue; and Step 1.7, enabling the UAV to return and land: automatically controlling the UAV to return to coordinates of a take-off point and land.

3. The method for detection of soil heavy metal pollution using an UAV and an XRF technology according to claim 1, wherein step 3 is specifically as follows:

assuming that there are n+1 linearly independent continuous functions:

$\varphi_0(x), \varphi_1(x) \ldots \varphi_n(x)$, wherein $\varphi_k(x)=x^k$, k=1, 2, . . . , n, $$p(x) = \sum_{k=0}^{n} a_k \varphi_k(x)$$

is recorded, namely: $p(x)=a_0+a_1x+\ldots+a_nx^k$, then a function p(x) is a linear function with respect to a coefficient dx, and for a set of known discrete data points $(x_0, y_0)$, $(x_1, y_1), \ldots,$ and $(x_m, y_m)$, a set of ax satisfying the following formula is solved:

$$I = \sum_{i=0}^{m} [p(x_i) - y_i]^2$$

then a least square fitting function of this set of discrete data is the function p(x), and to obtain a minimum I, conditions for an extreme value of a multivariate function are obtained:

$$\sum_{k=0}^{n} \left( \sum_{i=0}^{m} \varphi_j(x_i)\varphi_k(x_i) \right) \cdot a_k = \sum_{i=0}^{m} \varphi_j(x_i)y_i, \ j = 0, 1, \ldots, n,$$

and
assuming that $$(\varphi_i, y) = \sum_{k=0}^{m} \varphi_i(x_k)y_k, \ (\varphi_j, \varphi_k) = \sum_{i=0}^{m} \varphi_j(x_i)\varphi_k(x_i)$$

is recorded, then the above formula is transformed into:

$$\begin{bmatrix} n & \sum_{i=1}^{n} x_i & \cdots & \sum_{i=1}^{n} x_i^k \\ \sum_{i=1}^{n} x_i & \sum_{i=1}^{n} x_i^2 & \cdots & \sum_{i=1}^{n} x_i^{k+1} \\ \vdots & \vdots & \vdots & \vdots \\ \sum_{i=1}^{n} x_i^k & \sum_{i=1}^{n} x_i^{k+1} & \cdots & \sum_{i=1}^{n} x_i^{2k} \end{bmatrix} \begin{bmatrix} a_0 \\ a_1 \\ \vdots \\ a_n \end{bmatrix} = \begin{bmatrix} \sum_{i=1}^{n} y_i \\ \sum_{i=1}^{n} x_i y_i \\ \vdots \\ \sum_{i=1}^{n} x_i^k y_i \end{bmatrix},$$

through conversion to a Vandermonde matrix, the following is obtained:

$$\begin{bmatrix} 1 & x_1 & \cdots & x_1^k \\ 1 & x_2 & \cdots & x_2^k \\ \vdots & \vdots & & \vdots \\ 1 & x_n & \cdots & x_n^k \end{bmatrix} \begin{bmatrix} a_0 \\ a_1 \\ \vdots \\ a_n \end{bmatrix} = \begin{bmatrix} y_1 \\ y_2 \\ \vdots \\ y_n \end{bmatrix},$$

the formula is expressed for short as:
$X \cdot A = Y$, and by solving a coefficient matrix A, a fitting curve of the polynomial least squares method (PLSM) is obtained.

4. The method for detection of soil heavy metal pollution using an UAV and an XRF technology according to claim 2, wherein step 1.2 is specifically as follows:

Step 1.2.1, fitting an operation area to a closest polygon to obtain coordinates of each vertex of the closest polygon in the operation area;

Step 1.2.2, calculating a longest edge of the operation area according to coordinate information of the vertexes;

Step 1.2.3, constructing a route coordinate system: constructing a geodetic coordinate system and the route coordinate system based on the longest edge;

Step 1.2.4, performing coordinate system conversion: converting the coordinates of the vertexes from the geodetic coordinate system into the route coordinate system;

Step 1.2.5, performing route planning and task point coordinate acquisition: after the coordinate system is built, planning a route according to actual needs; and setting a distance between the routes and a distance between the task points, planning an UAV flight route parallel to the longest edge in the route coordinate system, and obtaining route coordinates of all the task points for data acquisition; and Step 1.2.6, constructing the task queue: starting from an origin, traversing all the task points along the route back and forth, converting the route coordinates of all the task points into geographic coordinates, and adding the geographic coordinates into the task queue successively.

5. The method for detection of soil heavy metal pollution using an UAV and an XRF technology according to claim 2, wherein step 1.4 is specifically as follows:

Step 1.4.1, reading geodetic coordinates of the next target point from the task queue, obtaining geodetic coordinates and Euler angle data of an initial position of the UAV from a flight control system, and converting the geodetic coordinates into a body coordinate system;

Step 1.4.2, after coordinate system conversion is completed, calculating expected moving distances Dx and Dy in X-axis and Y-axis respectively from coordinates of an initial point and the target point;

Step 1.4.3, setting an allowable error d and a step size s, wherein the allowable error d represents a maximum error allowed by the system, the UAV is considered to reach the target point when distance errors between positions of the UAV and the target point in both X-axis and Y-axis directions are less than d, and the step size s represents a maximum displacement of the system to adjust movement of the UAV each time;

Step 1.4.4, obtaining the geodetic coordinates and Euler angle data of a current position of the UAV through the flight control system, and converting the geodetic coordinates into the body coordinate system;

Step 1.4.5, calculating moving distances dx and dy of the UAV in the X-axis and Y-axis directions through the current position of the UAV and the initial position of the UAV, and calculating distances to be moved of the UAV dx, and dy$_0$ according to the expected moving distances and the moving distances;

Step 1.4.6, determining whether the current position of the UAV has reached the target point within the allowable error of the system, if so, ending a control method and enabling the UAV to hover over the target point to wait for a command, and if not, proceeding to the next step; and Step 1.4.7, determining whether the distance to be moved is less than the step size s in the X-axis and Y-axis directions respectively, if so, controlling the UAV to move a remaining distance in this direction in the next step, and if not, controlling the UAV to move a distance s in this direction; and after the movement is completed, returning to step 1.4.4.

6. The method for detection of soil heavy metal pollution using an UAV and an XRF technology according to claim 2, wherein step 1.5 is specifically as follows:

Step 1.5.1, descending in a first stage: in the first stage, controlling the UAV to descend to an altitude of $h_1$ according to the UAV's own GPS data and altitude data of a barometer;

Step 1.5.2, descending in a second stage: in the second stage, controlling the UAV to slowly descend to the altitude of $h_2$ based on altitude information of a current distance measurement sensor and the ground measured in real time by an altitude hold module of the system, wherein $h_2$ is the altitude for acquiring the soil data near the ground.

7. The method for detection of soil heavy metal pollution using an UAV and an XRF technology according to claim 4, wherein step 1.2.5 is specifically as follows:

performing route planning and task point coordinate acquisition: after the coordinate system is built, planning the route according to actual needs; and setting the distance between the routes and the distance between the task points, planning the UAV flight route parallel to the longest edge in the route coordinate system, and obtaining the route coordinates of all the task points for data acquisition; and calculating a largest Y-axis coordinate $y_{max}$=max ($y_{V1}$, $y_{V2}$, . . . , $y_{Vn}$) among the m vertexes of the polygon fitted in step 1.2.1, setting a distance D between two adjacent routes, and drawing a set of straight lines with a distance of D and parallel to $y_{V1}y_{V2}$ between y=0 and y=$y_{max}$; in XOY, reserving the route inside the polygon by calculating an intersection of the polygon fitted in step 1.2.1 and the set of straight lines to obtain the final UAV operation route; and after planning the route, determining a distance d between two adjacent task points in a route, traversing each route, determining the number of task points for each route by a formula (3), and distributing these task points uniformly on the route:

$$n_i = rund\left(\frac{x_{i2}x_{i1}}{d}\right) + 1,$$

in the formula, $n_i$ represents the number of task points on an i-th route, rund represents the rounding to the nearest integer, and $x_{i2}$ and $x_{i1}$ are X-axis coordinates of right and left endpoints of the route respectively.

8. The method for detection of soil heavy metal pollution using an UAV and an XRF technology according to claim 6, wherein step 1.5.1 is specifically as follows:

S1, reading information of $h_1$, $h_2$, allowable altitude error h, and allowable roll angle error r;

S2, obtaining geodetic coordinates and Euler angle data of a current position of the UAV, and converting the geodetic coordinates into a body coordinate system;

S3, calculating an expected displacement $Z_1$=H–$h_2$ through a current altitude of the UAV and $h_2$;

S4, obtaining, by the system, geodetic coordinates and Euler angle data of a current position of the UAV again, and converting the geodetic coordinates into the body coordinate system;

S5, reversely adjusting, by the system, a roll angle according to a current roll angle of the UAV;

S6, calculating and determining the remaining displacement $Z_2$=$h_{now}$–$h_2$ according to the current altitude of the UAV, wherein $h_{now}$ is the current altitude of the UAV;

S7, determining whether the remaining displacement is less than the allowable error h or a negative number, and if so, entering S10, otherwise entering step S8 and continuing execution;

S8, determining whether the remaining displacement is less than the set step size, and if so, descending the UAV by an altitude of z, otherwise descending the UAV by a maximum step size;

S9, recalculating the remaining displacement, and according to the different descending altitudes z being 0 or $Z_2$-s in the previous step, performing step S8 again; and S10, determining whether an absolute value of the current roll angle is within a range of the allowable error of the system, and if so, completing the first stage for control and entering the second stage, otherwise performing step S4.

9. The method for detection of soil heavy metal pollution using an UAV and an XRF technology according to claim 6, wherein step 1.5.2 is specifically as follows:

D1, obtaining real-time altitude data, and determining whether an absolute value of a difference between altitude data and a working altitude meets the allowable error of the system, and if so, waiting for subsequent data acquisition, otherwise continuing execution; and D2, calculating a smaller value of 0.05 m and 0.7 times the absolute value of the difference between the altitude data and the working altitude, then controlling the UAV to move down a distance of this smaller value, and performing step D1 after completion.

* * * * *